US009788743B2

(12) United States Patent
Burnham et al.

(10) Patent No.: US 9,788,743 B2
(45) Date of Patent: Oct. 17, 2017

(54) METHODS FOR USING A MULTIPLE ELECTRODE COMPOSITE SYSTEM IN ELECTROCARDIOGRAM DETECTION SYSTEMS

(71) Applicant: FLEXcon Company, Inc., Spencer, MA (US)

(72) Inventors: Kenneth Burnham, Warren, MA (US); Suraj Gorkhali, Spencer, MA (US); Andrew Greene, Leicester, MA (US)

(73) Assignee: FLEXcon Company, Inc., Spencer, MA (US)

( * ) Notice: Subject to any disclaimer, the term of this patent is extended or adjusted under 35 U.S.C. 154(b) by 718 days.

(21) Appl. No.: 14/304,238

(22) Filed: Jun. 13, 2014

(65) Prior Publication Data

US 2014/0296685 A1  Oct. 2, 2014

Related U.S. Application Data

(62) Division of application No. 12/536,068, filed on Aug. 5, 2009, now Pat. No. 8,792,957.
(Continued)

(51) Int. Cl.
*A61B 5/0408* (2006.01)
*A61B 5/0428* (2006.01)

(52) U.S. Cl.
CPC ........ *A61B 5/04087* (2013.01); *A61B 5/0408* (2013.01); *A61B 5/04085* (2013.01);
(Continued)

(58) Field of Classification Search
CPC ............ A61B 5/0408; A61B 2018/147; A61B 2018/167; A61B 5/04
(Continued)

(56) References Cited

U.S. PATENT DOCUMENTS 3,911,906 A  10/1975  Reinhold, Jr.
4,008,721 A   2/1977  Burton
(Continued)

FOREIGN PATENT DOCUMENTS

CA     2477615 A1    1/2006
CN  101188969 A    5/2008
(Continued)

OTHER PUBLICATIONS

English translation of the First Office Action issued by the State Intellectual Property Office of the People's Republic of China dated Oct. 9, 2015 in connection with related Chinese Patent Application No. 201410250452.5, 7 pages.
(Continued)

*Primary Examiner* — Joseph Stoklosa
*Assistant Examiner* — Brian M Antiskay
(74) *Attorney, Agent, or Firm* — Gesmer Updegrove LLP

(57) ABSTRACT

A biomedical sensor system is disclosed that includes a plurality of electrodes and a contiguous adhesive material that is in contact with each of the plurality of electrodes. In certain embodiments a method is provided that includes the step of applying a first surface of adhesive material to a patient wherein the adhesive material includes at least two electrodes on second surface thereof that is opposite the first surface. The method also includes the step of receiving a time varying signal a first electrode of the at least two electrodes at a first location such that the time varying signal is not received at a second electrode of the at least two electrodes.

19 Claims, 14 Drawing Sheets

Related U.S. Application Data

(60) Provisional application No. 61/086,601, filed on Aug. 6, 2008.

(52) U.S. Cl.
CPC ....... *A61B 5/04284* (2013.01); *A61B 5/04286* (2013.01); *A61B 2562/0209* (2013.01); *A61B 2562/046* (2013.01); *A61B 2562/125* (2013.01)

(58) Field of Classification Search
USPC .................... 600/372, 382, 386, 391–393
See application file for complete search history.

(56) References Cited

U.S. PATENT DOCUMENTS

| | | | |
|---|---|---|---|
| 4,063,352 A | | 12/1977 | Bevilacqua |
| 4,074,000 A | | 2/1978 | Hankee et al. |
| 4,293,665 A | | 10/1981 | Zalucha et al. |
| 4,352,359 A | | 10/1982 | Larimore et al. |
| 4,353,372 A | | 10/1982 | Ayer |
| 4,422,461 A | | 12/1983 | Glumac |
| 4,460,369 A | | 7/1984 | Seymour |
| 4,548,862 A | * | 10/1985 | Hartman ................. H01B 1/22 174/117 A |
| 4,581,821 A | | 4/1986 | Cahalan et al. |
| 4,798,773 A | | 1/1989 | Yasukawa et al. |
| 4,848,353 A | | 7/1989 | Engel |
| 5,120,325 A | | 6/1992 | Dow, Jr. |
| 5,120,422 A | | 6/1992 | Liu et al. |
| 5,143,071 A | | 9/1992 | Keusch et al. |
| 5,338,490 A | | 8/1994 | Dietz et al. |
| 5,362,420 A | | 11/1994 | Itoh et al. |
| 5,388,026 A | | 2/1995 | Kanbara et al. |
| 5,421,982 A | | 6/1995 | Ikeda et al. |
| 5,450,845 A | * | 9/1995 | Axelgaard ........... A61B 5/0408 600/382 |
| 5,645,062 A | | 7/1997 | Anderson et al. |
| 5,800,685 A | | 9/1998 | Perrault |
| 6,121,508 A | | 9/2000 | Bischof et al. |
| 6,134,480 A | * | 10/2000 | Minogue .............. A61N 1/0452 600/391 |
| 6,214,251 B1 | | 4/2001 | Wu et al. |
| 6,232,366 B1 | | 5/2001 | Wang et al. |
| 6,327,487 B1 | | 12/2001 | Stratbucker |
| 6,342,561 B1 | | 1/2002 | Engel et al. |
| 6,576,712 B2 | | 6/2003 | Feldstein et al. |
| 7,076,282 B2 | | 7/2006 | Munro et al. |
| 2002/0037977 A1 | | 3/2002 | Feldstein et al. |
| 2004/0000663 A1 | | 1/2004 | Segall et al. |
| 2004/0073104 A1 | | 4/2004 | Brun Del Re et al. |
| 2004/0210122 A1 | | 10/2004 | Sieburg |
| 2005/0107714 A1 | | 5/2005 | Matsumura et al. |
| 2006/0069320 A1 | | 3/2006 | Wolff et al. |
| 2006/0074284 A1 | | 4/2006 | Juola et al. |
| 2007/0010750 A1 | | 1/2007 | Ueno et al. |
| 2008/0208063 A1 | | 8/2008 | Brauers et al. |
| 2008/0311378 A1 | * | 12/2008 | Simpson ................ C08J 9/0066 428/319.1 |
| 2010/0016702 A1 | | 1/2010 | Greene et al. |
| 2010/0036230 A1 | | 2/2010 | Greene et al. |
| 2014/0221807 A1 | * | 8/2014 | Park .................... A61B 5/04 600/393 |
| 2014/0296684 A1 | | 10/2014 | Burnham et al. |

FOREIGN PATENT DOCUMENTS

| | | |
|---|---|---|
| DE | 199 22 999 A1 | 11/2000 |
| EP | 1 674 036 A1 | 6/2006 |
| GB | 2115431 | 9/1983 |
| JP | 2001-078974 | 3/2001 |
| JP | 2005-110801 A1 | 4/2005 |
| WO | WO9531491 | 11/1995 |
| WO | WO9724149 | 7/1997 |
| WO | 2005/032268 A1 | 4/2005 |
| WO | 2006131855 A1 | 12/2006 |
| WO | 2010009385 A1 | 1/2010 |

OTHER PUBLICATIONS

European Communication issued by the European Patent Office dated Jul. 5, 2016 in European Application No. 14178851.3.
European Communication issued by the European Patent Office dated Jul. 14, 2016 in European Application No. 09791176.2.
Office Action issued by the Canadian Patent Office dated Jun. 16, 2016 in Canadian Application No. 2731697.
Canadian Office Action issued Canadian Patent Office dated Apr. 27, 2017 in related Canadian Patent Application No. 2,731,697.
Search Report issued by the Canadian Intellectual Property Office dated Aug. 17, 2015 in connection with Canadian Patent Application No. 2,731,697, 1 page.
International Search Report and Written Opinion issued in related International patent application No. PCT/US2009/052815 dated Feb. 4, 2010 (19 pages).
International Preliminary Report on Patentability issued in International patent application No. PCT/US2009/052815 on Feb. 17, 2011 (10 pages).
European Patent Office Communication issued in related European patent application No. 09791176.2-1660 dated Nov. 21, 2014 (4 pages).
Search Report issued in related European patent application No. 14178851.3-1660 dated Nov. 28, 2014 (7 pages).
Office Action issued in related Indonesian patent application No. W-00201100476 dated Jul. 3, 2014 (and partial translation thereof) (5 pages).
Notice of Submission of Opinion/Office Action issued in related Korean patent application No. 10-2011-7002359 on Jan. 16, 2015 (translation included) (9 pages).
Australian Patent Report No. 2 issued in related Australian patent application No. 2009279710 dated Aug. 27, 2013 (2 pages).
Canadian Office Action issued by the Canadian Intellectual Property Office dated Jun. 9, 2015 in connection with Canadian Patent Appln. No. 2,730,507, (5 pages).
English Translation of the Final Office Action issued by the Korean Intellectual Property Office dated Jul. 28, 2015 in connection with Korean Patent Appln. No. 10-2011-7002866, (2 pages).
International Search Report and Written Opinion dated Dec. 16, 2009 in connection with International Application PCT/US2009/050979, (18 pages).
International Preliminary Report on Patentability dated Jan. 18, 2011 in connection with International Application PCT/US2009/050979, (10 pages).
Office Action, and partial translation thereof, issued by Japanese Patent Office in related Japanese Patent App. No. 2011-518934 dated Nov. 4, 2014.
Cover page of EP2312998, which corresponds to the above-mentioned US20100016702 and EP 2799007.
First Chinese Office Action issued by the State Intellectual Property Office of the People's Republic of China dated Oct. 10, 2012 in connection with Chinese Patent Appin. No. 200980128654.X, 11 pages.
First Australian Patent Office Examination Report dated Nov. 3, 2012 in connection with Australian Patent Application No. 2009279710, 4 pages.
International Preliminary Report on Patentability for PCT/US09/050979 filed on Jul. 17, 2009, 9 pages.
English Translation of the Japanese Office Action dated Nov. 19, 2013 in connection with Japanese Application No. 2011-518934, 1 page.
Australian Patent Office Examination Report dated Aug. 27, 2013 in connection with Australian Application No. 2009279710, 2 pages.
Second Office Action issued by the State Intellectual Property Office of the People's Republic of China and English translation thereof, dated Jun. 27, 2013 in connection with Chinese Application No. 200980128654.X, 6 pages.

(56) References Cited

OTHER PUBLICATIONS

International Preliminary Report on Patentability for PCT/US2009/052815 filed on Aug. 6, 2009, 10 pages.
"A direct comparison of wet, dry and insulating bioelectric recording electrodes," Searle et al. Physiological Measurement, Institute of Physics Publishing, Bristol, GB. vol. 21, No. 2. p. 271-283. May 1, 2000.
English Translation of the Chinese Office Action dated May 6, 2013 in connection with Chinese Patent Application No. 200980130966.4 filed on Aug. 5, 2009, 5 pages.
English Translation of Japanese Notice of Rejection dated Jan. 7, 2014 in connection with Japanese Patent Application No. 2011-522210, 1 page.
First Australian Patent Office Examination Report dated Sep. 4, 2012 in connection with Australian Patent Application No. 2009279810, 4 pages.
European Patent Office Communication Pursuant to Article 161(1) and 162 EPC dated Mar. 2, 2011 in connection with European Application No. 09790578.0, 2 pages.
International Search Report and Written Opinion dated Oct. 5, 2009 in connection with International Application PCT/US2009/050979, 18 pages.
European Patent Office Communication Pursuant to Article 94(3) EPC dated Mar. 8, 2012 in connection with European Application No. 09791176.2, 5 pages.
International Search Report and Written Opinion dated Oct. 23, 2009 in connection with International Application PCT/US2009/052815, 19 pages.
First Office Action issued by the State Intellectual Property Office of the People's Republic of China, dated Sep. 5, 2012 in connection with Chinese Application No. 200980130966.4, 7 pages.

\* cited by examiner

METHODS FOR USING A MULTIPLE ELECTRODE COMPOSITE SYSTEM IN ELECTROCARDIOGRAM DETECTION SYSTEMS

PRIORITY INFORMATION

The present application is a divisional application of U.S. application Ser. No. 12/536,068 filed Aug. 5, 2009, which claims priority to U.S. Provisional Patent Application Ser. No. 61/086,601 filed Aug. 6, 2008, the disclosures of which are hereby incorporated by reference in their entirety.

BACKGROUND OF THE INVENTION

The invention generally relates to sensor systems for detecting electrical signals within subjects, and relates in particular to electro-cardiogram detection systems.

Conventional electro-cardiogram (ECG) systems generally include an electrically conductive material that provides a conductive path between a surface of a subject and medical instrumentation. Sensors for use in biomedical applications such as ECG applications, are disclosed for example, in U.S. Pat. No. 4,848,353, which discloses an electrically-conductive, pressure sensitive adhesive; U.S. Pat. No. 5,800,685, which discloses an electrically conductive adhesive hydrogel; and U.S. Pat. No. 6,121,508, which discloses a conductive hydrophilic pressure sensitive adhesive. FIG. 1, for example, diagrammatically shows a conductive sensor device 10 of the prior art that includes an ionically conductive adhesive 12, a conductive electrode 14, and a supporting substrate 16. The ionically conductive adhesive 12 is applied to a patient, and electrical signals within the patient underlying the adhesive 12 travel through the adhesive 12 to the conductive electrode 14, which is electrically coupled to monitoring equipment. Certain ECG systems, for example, employ an ionically conductive hydrogel that includes water soluble salts dispersed therein, and in certain systems, these hydrogels are formulated to also function as the skin attachment adhesive.

Such hydrogels typically contain some amount of water within a gel and require that the material be maintained in a sealed environment (e.g., in sealed packages) until being used. Such materials are generally not re-usable in environments where the humidity is not closely controlled. These limitations adversely affect both the cost of sensors that use such conductive adhesives as well as the amount of use that any particular sensor may enjoy.

The hydrogels perform as signal receptors via an ionically conductive mechanism and are therefore low impedance receptors. For example, the conductive electrode may include silver and silver chloride (Ag/AgCl), which typically has a sheet resistance of between 0.1 and 0.5 Ohms/sq-mil. The units Ohms/sq/mil are conventionally used to refer to surface resistivity (Ohms/square) over a volume, yielding Ohms/sq-mil. The conductive layer is deposited over a conductive carbon coated polymeric film (typically having an impedance range of between 1-1000 Ohms/sq/mil) and a conductive lead that is used to couple the electrode to monitoring equipment. The electrode layer serves as a transducer between the ionically generated biological signal and the electrical signal transmitted in the conducting solution. The chloride serves as the ion in the electrolyte. Current flows freely across the electrode because the Ag/AgCl chemical structures are stable.

When the hydrogel of an electrode is placed in contact with the skin, ions will diffuse into and out of the metal via the hydrogel. Copper has an electrode potential of 340 mV, which is a greater potential than exists in an ECG signal (~1 mV). The reference electrode should therefore, cancel this potential, but in practice this is not the case. Electrode potentials change with time due to the ionic interaction. Also, any two electrodes and the underlying skin surfaces are not identical. For these reasons the electrode potentials differ. The electrode potentials appear as signal offset. Silver chloride (AgCl) has a potential of under 5 mV, which is easily handled by typical monitoring technology and will not interfere with the ECG signal. For this reason the AgCl produces low levels of noise (less than 10 µV) which is ideal for the ECG application since the amplitude of the heart palpitations that are required to be transmitted to the monitoring equipment.

The number of signal detecting devices used in a harness system may typically range from 3 to 13 electrodes or more. Employing a larger number of detection points provides that many points of reference are available for monitoring a subject, such as a patient's heart. As shown in FIG. 2, some ECG harness systems provide ten or more receptors (electrical contacts) 20 that are coupled to a common harness 22 that leads to an ECG device (not shown) via a connector 24. Harness systems such as shown in FIG. 2 may be easier to hook-up to the ECG monitor than separately-wired sensors, and may be more comfortable for the patient as well as more securely attachable to the patient. Because the hydrogels are low impedance therefore, the ECG harness systems must also be low in electrical impedance.

U.S. Patent Application Publication No. 2004/0000663 discloses a water insensitive alternating current responsive composite that may be used as an adhesive or a polymeric film in a sensor, and provides that an alternating current signal on one side of the composite may be capacitively coupled to the other side of the composite by having the dielectric properties of the material change with the application of an alternating current field (e.g., exhibits dielectric dispersion) such that a charge is released from the composite at the other side of the composite responsive to the changing dielectric properties. The signal receptive materials of U.S. Patent Application Publication No. 2004/0000663 are disclosed to have impedance values of about 100 kΩ or higher.

There remains a need, however, for inexpensive yet effective biomedical sensor harness and wiring systems that may be easily and economically employed in a variety of applications, and that provide improved sensitivity and useful information to a wide variety of medical personnel.

SUMMARY

In accordance with certain embodiments, the invention provides a biomedical sensor system that includes a plurality of electrodes and a contiguous adhesive material that is in contact with each of the plurality of electrodes. In some embodiments a method is provided that includes the step of applying a first surface of adhesive material to a patient wherein the adhesive material includes at least two electrodes on second surface thereof that is opposite the first surface. The method also includes the step of receiving a time varying signal a first electrode of the at least two electrodes at a first location such that the time varying signal is not received at a second electrode of the at least two electrodes.

In accordance with further embodiments, the invention provides a method of detecting a time varying signal from a patient that includes the steps of applying a first surface of adhesive material to a patient, wherein the adhesive material is provided at a thickness of less than about 50 microns yet provides total peel strength of at least about 6000 gram seconds, and receiving a time varying signal at a first electrode that is in contact with the adhesive material. In further embodiments, a plurality of electrodes are provided on a second surface of the adhesive material, and the step of receiving the time varying signal at the first electrode involves not receiving the time varying signal at a second electrode that is separated from the first electrode by a distance of less than about 2,500 microns.

BRIEF DESCRIPTION OF THE DRAWING

The following description may be further understood with reference to the accompanying drawings in which.

Figure 1:
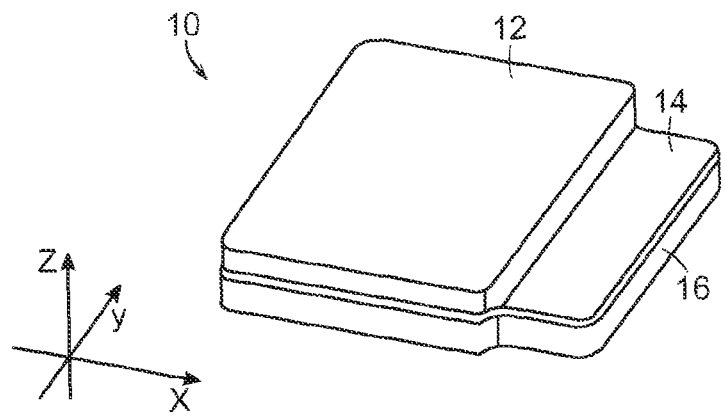
FIG. 1 shows an illustrative diagrammatic view of a biomedical sensor of the prior art.
Figure 2:
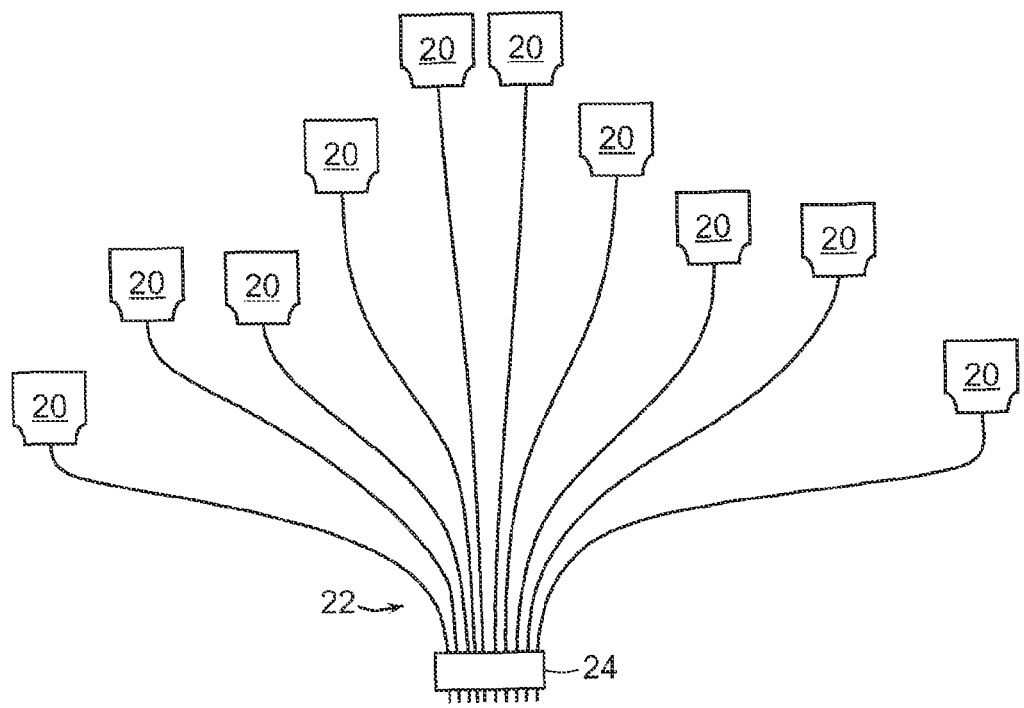
FIG. 2 shows an illustrative diagrammatic view of a biomedical sensor harness system of the prior art.

The drawings are shown for illustrative purposes and are not to scale.

DETAILED DESCRIPTION

It has been discovered that a high impedance continuous signal receptive material may be provided in accordance with the invention that may serve as a common attachment adhesive for multiple high impedance electrodes, for example, covering an array of sites, and further that an inexpensive high impedance connection system may be used with the multiple high impedance electrodes. The signal receptive material (SRM) is a high impedance (e.g., greater than 20 k$\Omega$/sq.-mil) material that is responsive to a localized time varying signal, yet does not permit ionic conductivity throughout the material. Many advantages may be provided by such a system. A first of such advantages is simplicity of manufacturing. It is not necessary to register (align) the SRM to the individual electrodes. Instead, multiple electrodes may be placed on a common SRM. An additional benefit is that the increased adhesive area may allow for an optimal bond to the patient. The use of high impedance electrodes (e.g., greater than 50 k$\Omega$/sq.-mil), and connection systems (e.g., greater than 50 k$\Omega$/sq.-mil) also facilitate reducing the overall system cost and complexity of the electrodes. A flexible substrate could also be used as a supporting structure, and such a supporting substrate could be conformable and water vapor and oxygen permeable. Such substrate materials are commonly found for example, in medical applications for use in wound dressings and surgical drapes.

As mentioned above, a technical problem that prevents conductive composites such as hydrogel adhesives from being used in such a way is the fact that the hydrogels have low impedance along the X, Y, and Z dimensions. Thus, if such an adhesive were to span across two or more conductive electrode sensors, any signal generated at one site might be conveyed over the mass of the hydrogel, thus losing the signal specificity to a particular site. For a material to function properly in such an application it would have to have high internal impedance yet still be capable of detecting a biomedical signal and conveying some representative signal to the site specific electrodes.

In accordance with the invention, a high impedance sensor is employed, such as a sensor that is dielectric yet changes its dielectric properties in the presence of biomedical signals, which are typically time varying signals such as alternating current signals. Such a sensor may include a polymeric material and a polar material that is substantially dispersed within the polymeric material as disclosed, for example, in U.S. Patent Application Publication No. 2004/0000663, the disclosure of which is hereby incorporated by reference in its entirety. Using the testing protocol that is described therein, such an adhesive may be provided. An example of such a polymeric material with a polar material substantially dispersed within the polymeric material is, for example, the EXH 585 adhesive product as sold by FLEXcon Company, Inc. of Spencer, Mass. This adhesive exhibits resistance values of about 200,000 Ohms. By comparison, hydrogels exhibit resistance values of less than 3,000 Ohms (for an individual electrode pair) as required by the American National Standards Institute and the Association for the Advancement of Medical Instrumentation (ANSI/AAMI) in accordance with standard EC12 for disposable ECG electrodes. Conventional hydrogels, in fact, must be more conductive than a patient's skin in order to function properly.

Utilizing the selection methods stated within U.S. Patent Application Publication No. 2004/0000663 for compatibility, organo-salts may be provided within the continuous polymeric medium. Non-tacky variants may also be formulated to have the same capacitive coupling, and thus signal responsive characteristics, as thermally activated adhesive systems. Non-pressure sensitive adhesive (non-PSA) variants may have desirable characteristics in some sensing applications, where the adhesion properties may not be needed or be desirable, such as, for example, a sensor array where the test subject is placed on top of the array and there is little to no movement of the test subject during the test.

To determine the impedance of a conventional hydrogel and for a sample of the above mentioned EXH 585 product, an HP 33120A Waveform Generator (as sold by Hewlett Packard Company of Palo Alto, Calif.), creating a 10 Hz sinusoidal waveform signal was used. This signal was then passed through a test sample meeting the ANSI/AAMI EC-12 specification, adhesive to adhesive configuration for tab electrodes. The response signal was received by a BK Precision 100 MHz Oscilloscope model 2190 as sold by B&K Precision Corporation of Yorba Linda, Calif. The resulting waveform display was compared to those produced from tests of various known resistances until an equivalent matching waveform was obtained. The known resistance value that produced the waveform exhibiting the best match to the test sample was then taken as the equivalent matching resistance value for that test sample.

The present invention provides that a contiguous high impedance signal receptive material (SRM) may be used that has many signal detection sites, and further that a high impedance connection system may be employed. Again, some advantages of such a system include ease of application to the patient, better total adhesion to the patient due to greater total bonding area, significantly less a chance of any single electrode coming loose, and the opportunity for using multiple site positions, whether or not in a defined combination, to yield a more accurate profile of, for example, the electrical activity of a patient's heart.

Another advantage in using high impedance SRM that does not use an ionic conductive mechanism to conduct biomedical signals is that it allows a lower cost conductive structure to be used for signal transmission. The need for a silver/silver chloride contact electrode is avoided and lower cost contacts such as vacuum deposited aluminum or a conductive carbon coating, or for that matter most conductive contact materials would be fully functional for use with the SRM.

Figure 3A:
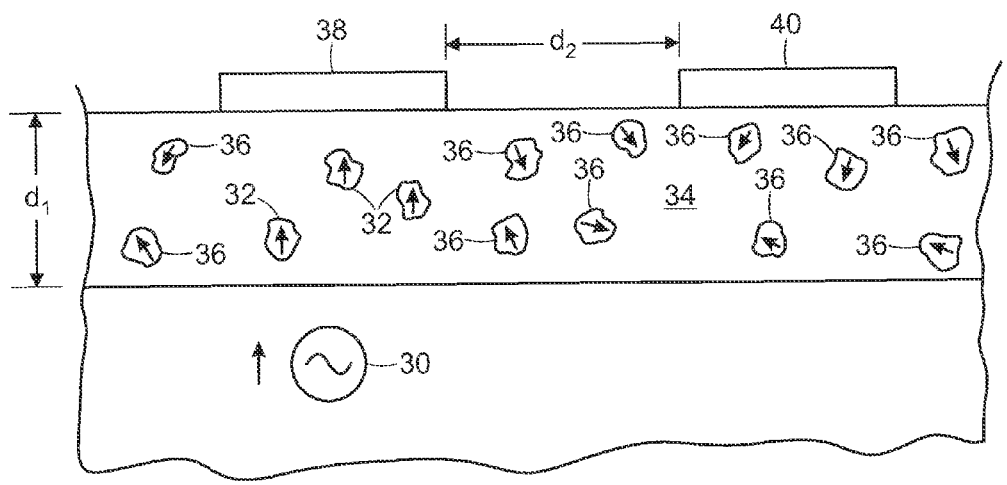
FIGS. 3A and 3b show illustrative diagrammatic views of a sensor system in accordance with an embodiment of the invention during use.
Figure 3B:
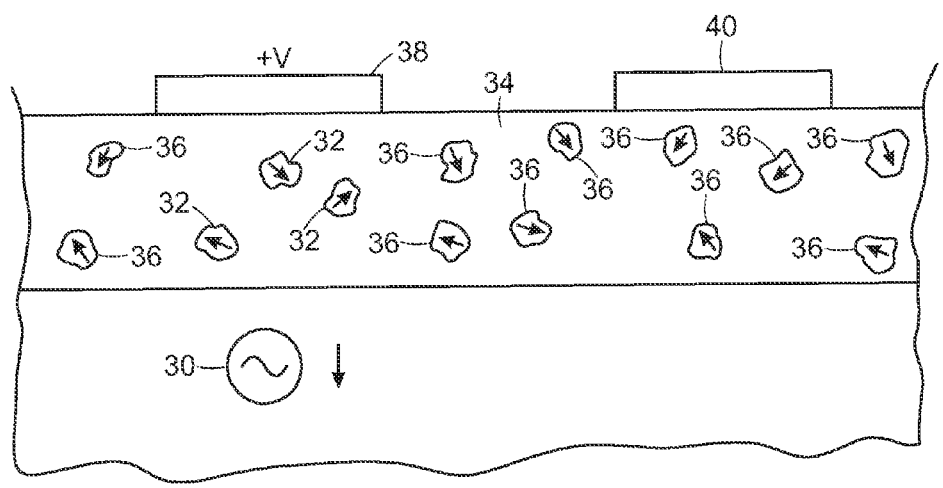

FIGS. 3A and 3B show illustrative views of a signal receptive material of the invention in which a biomedical signal (e.g., a time varying signal such as an alternating current signal) within a subject, such as a patient's heart, is represented at 30. In FIG. 3A, the biomedical signal at 30 is rising in amplitude, and in FIG. 3B, the biomedical signal at 30 is falling in amplitude.

When the biomedical signal 30 rises in amplitude, polar material 32 dispersed within a polymer 34 that is between the biomedical signal at the surface of the subject and a high impedance electrode 38 becomes aligned with the biomedical signal, while polar material 36 that is not immediately adjacent to the biomedical signal and the high impedance electrode 38 does not become aligned. In particular, when the polar material 32 becomes aligned as shown in FIG. 3A, the dielectric properties of the polymer matrix 34 in the area of the aligned polar material 32 change.

As shown in FIG. 3B, when the biomedical signal falls in amplitude, a small signal is discharged from the area of the formerly aligned polar material 32 due to the relaxation of polarization of the dielectric material. This small signal is passed by a high impedance conductor 38 to a detection circuit. If another high impedance conductor 40 is nearby the high impedance conductor 38, it will not receive a charge because the polar material near the high impedance conductor 40 does not align responsive to the signal 30. In this way, high impedance conductors may be placed very close to one another without mutual interference. For example, one may specify that the distance between high impedance conductors 38 and 40 ($d_2$ as shown) should be at least as large as the thickness ($d_1$) of the polymer matrix that includes the polar material.

In this way, a representative output signal is generated that is representative of the original biomedical signal at a specific site. The representative output signal is generated responsive to changes in the dielectric properties of the composite material (the SRM), and the dielectric properties are changed responsive to the presence of a time varying signal from within the subject. Because the SRM is not conductive, but is instead a dielectric, multiple sensor conductors may be placed near each other on a continuous SRM. The SRM, therefore, exhibits dielectric dispersion in a subset area of the SRM rather than over the entire SRM responsive to a signal that is local to the subset area.

Figure 5:
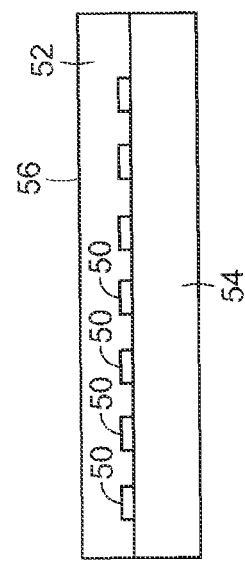
FIG. 5 shows an illustrative diagrammatic side view of the sensor system of FIG. 4.
Figure 4:
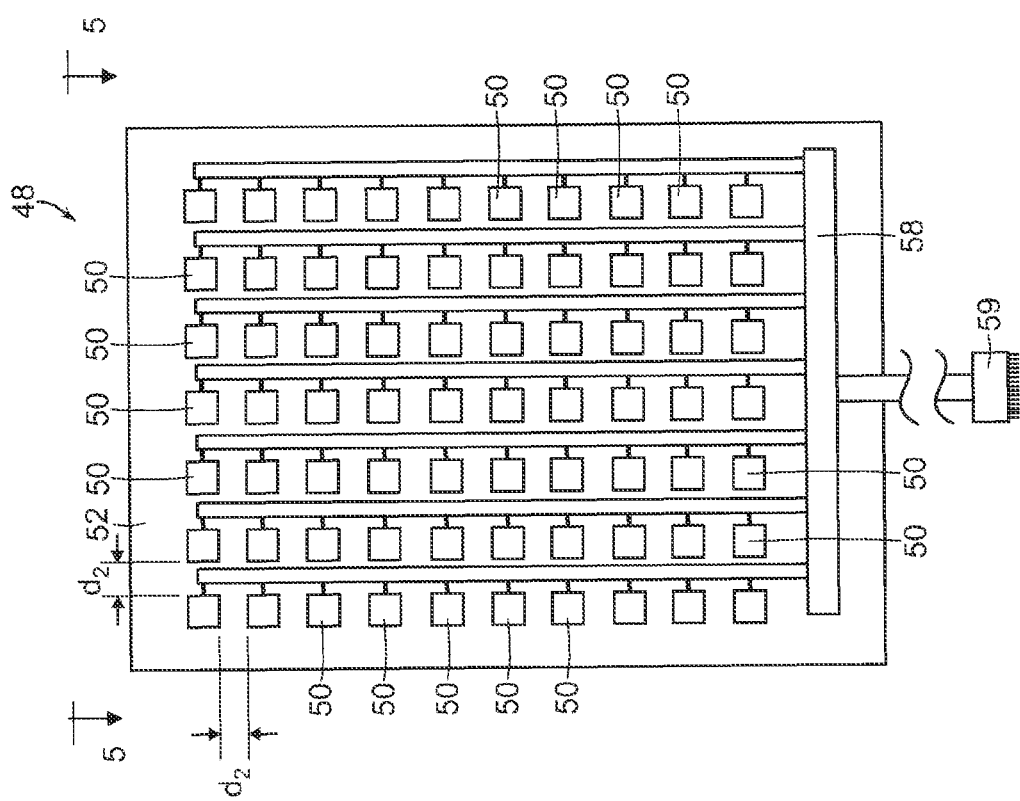
FIG. 4 shows an illustrative diagrammatic plan view of a sensor system in accordance with an embodiment of the invention that includes an electrode array.

FIGS. 4 and 5 a multi-site sensing array 48 that may be provided using a high impedance SRM in accordance with an embodiment of the invention in which an array of high impedance electrodes 50 is provided on a continuous SRM material 52 as described above. FIG. 4 shows a top view through a transparent SRM material 52, and FIG. 5 shows a side view thereof taken along line 5-5 of FIG. 4. Such an array may be used in applications such as ECG monitoring as well as a wide variety of other medical and non-medical applications. As also shown in FIG. 4, the high impedance electrodes and SRM composite may be supported by a releasable support substrate or carrier 54 that is separated from the SRM 52 and high impedance electrodes 50 following application of the exposed surface 56 of the SRM to a patient.

While FIGS. 4 and 5 show a multi-Sensor Pad array, other layouts may also be provided. Data received from such a dense array of sensors may be provided for example, at a connector 69 using collection bus 58 fed by auxiliary buses or by a conventional multiplexing method. The selection of which of the sensing pads are active may be programmed in, or may be determined automatically by an algorithm or other method of information processing analysis, even after the array is applied. The active pad configuration could be changed anytime during the monitoring cycle. Thus the signal receptors may be selectively chosen in order to provide the diagnostician with the optimal viewing angle for a specific palpitation. Viewing angle accuracy and control through this vector method is greatly improved. The possibility of a shorted or improperly connected receptor contaminating an accurate measurement would be greatly reduced.

The choice of the SRM, such as discussed above or any other similar SRM is based on two fundamental properties: 1) High impedance, such as for example, impedance greater than 200,000 Ohms measured as per American National Standard for Pregelled ECG Disposable Electrodes (ANSI/AAMI EC12); and 2) That the mechanism of signal transfer is not a function of ionic conductivity. This enables having, for example, a single SRM layer and multiple sensing pads leading to multiple conductive pathways, without having the signals interfere with one another. Capacitive coupling needs a conductive layer (other than a patient's body for example) to complete a capacitive structure, thus allowing for the option of having the SRM layer continuously extending across more than one sensing pad. This is not possible with low impedance, ionically conductive hydrogels.

For thin high impedance conductive coatings, such as printed lead wires or printed high impedance electrodes, surface resistivity characterizes the impedance. As discussed above, the surface resistivity of materials is reported in units of $\Omega$/square area. The square is a dimensionless unit representing an area equal to the square of the width of the thin coating ($W^2$). Typically those skilled in the art normalize this value to a coating with a thickness of 1 mil (0.001 inches), resulting in unit of $\Omega$/sq-mil (Ohms per square per mil). Knowledge of a material's surface resistivity allows the calculation of the resistance for a given thin deposit of that material. For example:

$R_s$=surface resistivity in $\Omega$/sq
$R_v$=volume resistivity in $\Omega$/sq-mil
T=coating thickness in mils
L=length in mils
W=width in mils
$R=R_s \times (L/W) \times (1/T)$ The use of the high impedance SRM in the area of bio-medical monitoring has several advantages. First, the high impedance electrode may be composed of lower cost materials rather than materials including costly silver/silver chloride. Further the use of non-metallic higher impedance conductors, to form the high impedance output contacts leading to the ECG monitor, would be acceptable. High impedance materials such as, but not limited to, a conductive carbon coating product from FLEXcon such as their EXV-216, or intrinsically conductive polymers such as the CLEVIOS family of products sold by H.C. Stark GmbH of Germany, or carbon nanotube dispersions such as Super HiPCO nanotubes available from Carbon Nanotechnologies, Incorporated of Houston, Tex., could be substituted for the silver/silver chloride electrode of the prior art. Both the high impedance electrodes and the high impedance output contacts may be printed on a common supporting substrate. Further cost savings may be obtained from the ease of manufacturing as well as reduced thickness of the SRM. The distance between electrodes ($d_2$) as shown in FIG. 4 may be for example, less than about one inch (25,000 microns), and preferably may be less than about 100 mil (2,500 microns). In further embodiments, the distance $d_2$ may be substantially the same as the thickness of the SRM (e.g., less than about 200 microns) as discussed above.

Because multiple high impedance electrodes may be placed on a continuous SRM, registration to a specific electrode is not as critical as is the case with an ionically conductive hydrogel, which may reduce manufacturing costs. Also, the thickness of an SRM which operates through capacitive coupling may be less than that of an ionic electrolyte (e.g., hydrogel), which is often 300-625 microns thick. This extra hydrogel mass helps ensure a gap free skin contact, as well the ability to pick up the signals from the heart. In contrast, the intrinsic adhesion of the capacitively coupled SRM is more a function of the polymer base chosen. Thus adhesion may be better tailored to the needs of the application and the signal pickup is not a function of adhesive mass. The thickness of the SRM may, therefore, be for example between about 5 microns and about 200 microns. This provides, that the resulting biomedical sensor device (including a high impedance conductor, a dielectric material and an optional support material) may have a total thickness of less than about 250 microns, which is less than the thickness of a conventional hydrogel alone. In further embodiments, the thickness of the SRM may preferably be between about 25 microns and about 100 microns.

In fact there are advantages with respect to improved defibrillation overload recovery performance when using a thinner layer of the SRM (preferably 25-100 microns), consistent with maintaining adequate contact to the patient's skin. Thinner layers of the SRM would, of course, have cost advantages. These advantages would still be maintained even over a wider bonding area. The cost reduction motive has lead to the use of less and less contact area to save on the hydrogel and the silver/silver chloride cost. Using a capacitively coupled SRM, at a thinner, 5-200 microns deposition, even over a greater surface area, would still maintain a significant material and manufacturing cost advantage. Beside the economic advantage of using a low deposition of the signal receptive material, using a thinner signal receptive material provides for a greater anisotropic effect.

Figure 6:
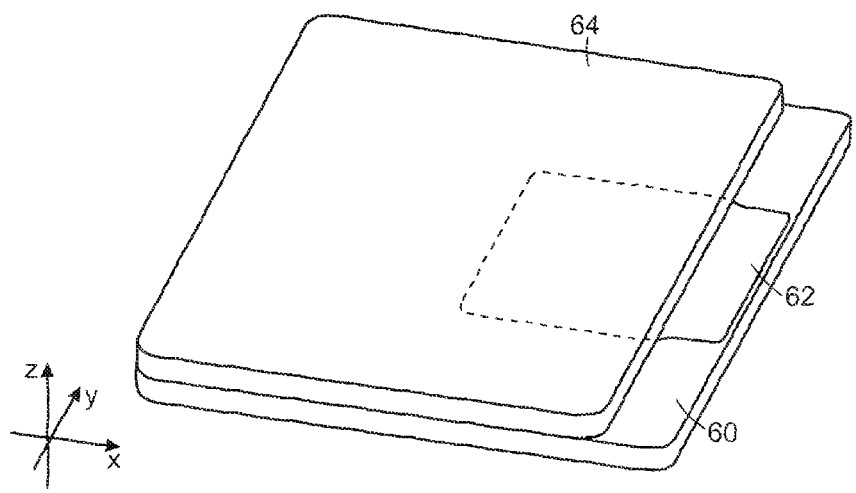
FIG. 6 shows an illustrative diagrammatic isometric view of a sensor system in accordance with an embodiment of the invention.

This cost advantage would be maintained even if the area of the SRM is greater than the area of the high impedance electrode. As shown in FIG. 6, a supporting substrate 60 on which a high impedance electrode 62 and signal receptive material 64 are applied may include much more supporting substrate and SRM than required; the SRM extends beyond the boundaries of the conductive electrode sensor. This configuration allows more control of adhesion of the electrode when the SRM is serving as the attachment adhesive as well as the signal receptive medium. It should be noted that if a typical hydrogel were so extended over the electrode, additional signals from the extra area covered by the hydrogel would cause some alteration in the position specificity of the ECG sensor. Thus, using a hydrogel extension to improve adhesion to the patient would have more than just a cost penalty.

Figure 7:
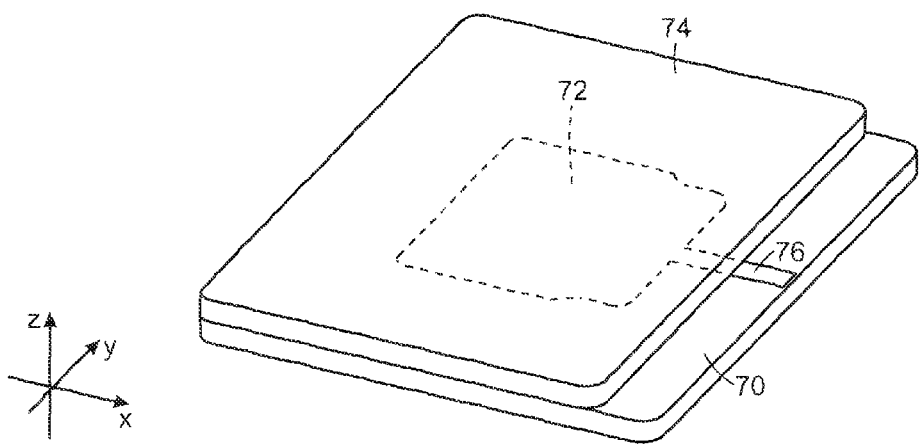
FIG. 7 shows an illustrative diagrammatic isometric view of a sensor system in accordance with another embodiment of the invention.

As shown in FIG. 7, the high impedance electrode sensor 72 may also be positioned well within the central region of the supporting substrate 70 and SRM 74 since any additional impedance of the lead 76 from the sensor 72 will not adversely impact reception of an output signal from the high impedance SRM material, provided that the ratio of the total area of the lead to the area of the electrode is small. If the ratio of areas $A_{lead}/A_{electrode}$ is larger than a critical ratio at which the lead itself may act as an effective electrode and pick up signals from areas away from the electrode, then a layer of insulating material or dielectric material of sufficient thickness may be disposed in alignment with the leads between the lead and the SRM to minimize or eliminate signal reception by the lead itself. The use of a high impedance SRM would not yield problems with signal fidelity.

Further the devices of FIGS. 6 and 7 would have the electrode and the surrounding skin better immobilized by the supporting substrate and the SRM. Thus inadvertent lifting of an edge of the electrode, or skin movement around the electrode, each of which may cause monitoring errors, may be minimized. An attempt to provide the same construction with a conventional ionically conductive hydrogel having a lower impedance adhesive, would permit signals generated from movements of the body around the electrode to be conducted in the X, Y plane of the hydrogel to the electrode.

An additional advantage of certain devices of the invention is that application of an array of electrodes on a continuous membrane to a patient, such as shown in FIGS. 4 and 5 using a continuous coating of high impedance SRM, would allow less adhesive thickness, and a less intrinsically tacky adhesive to be used. Adhesion to the patient would then be a function of total bond area, and would cause less discomfort to the patient upon removal.

Also, since such a system operates by capacitive coupling, the signal transmitted possesses low current characteristics, permitting the system to possibly be more desirable in electrical shunting conditions such as a defibrillation event. The high impedance electrode as well as the trace impedances may also serve to shield the patient and the medical personnel from excess current exposure.

Additionally, the possibility of multi-sensing electrodes (as shown in FIGS. 4 and 5), would allow a greater number of viewing angles that may aid signal detection and help a technician discern valid signals from external noise. This would also allow automated selection of which sensors are to be engaged.

Also, the ability to use higher impedance electrodes also provides that lower total metallic content may be employed, including the output leads to the ECG monitor and of the total electrode (plus SRM), lessening the requirement that the electrodes would have to be removed prior to other diagnostic tests such as X-ray, computer-aided tomography scans (CAT scans) and magnetic resonance imaging (MRI) analyses. Also, using non-metallic high impedance electrodes and output leads avoids many disposal problems concerning metals and metal salts.

An example of a sensor system of the invention that includes non-silver and silver chloride may be provided as follows. An ECG sensing electrode was constructed with the EXH-585 SRM material from the FLEXcon Company, Inc. of Spencer Mass. This adhesive operates via a non-ionic, capacitive coupling mechanism. The adhesive thickness was 25 microns, and applied to a 25 micron polyester film coated, on one side, with a conductive carbon coating (EXV-216 product from the FLEXcon Company) to a deposition of 25 microns, with an area of the conductively coated polyester not covered with the EXH-585 to allow an electrical contact to be made. The other end of the contact was to a GE Medical Systems model MAC 1200 ECG monitor. Three such pads were constructed and placed on a test subject, and an ECG reading was taken.

Figure 8A:
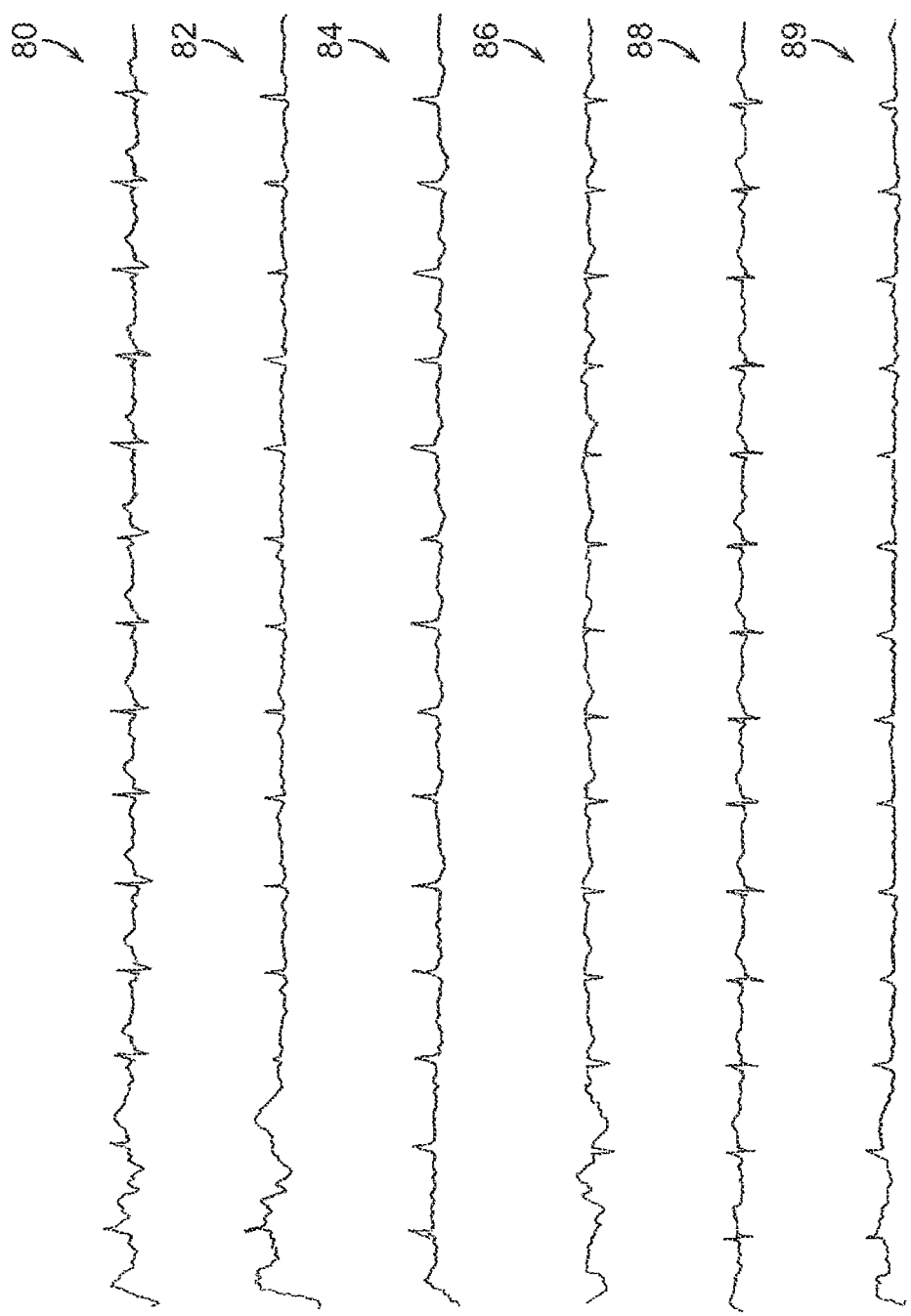
FIGS. 8A and 8B show illustrative graphical representations of ECG signals obtained from a system of the invention and a system of the prior art respectively.

FIG. 8A shows a sensor output that was provided by an ECG monitor representing certain portions of a composite signal, including for example, signals from the I, II, and III leads, as well as signals from the AVR, AVL and AVF leads. FIG. 8A shows the outputs of the I, II, III, AVR, AVL and AVF leads at 80, 82, 84, 86, 88 and 89 respectively for a subject using an SRM material as disclosed above in accordance with the invention.

Figure 8B:
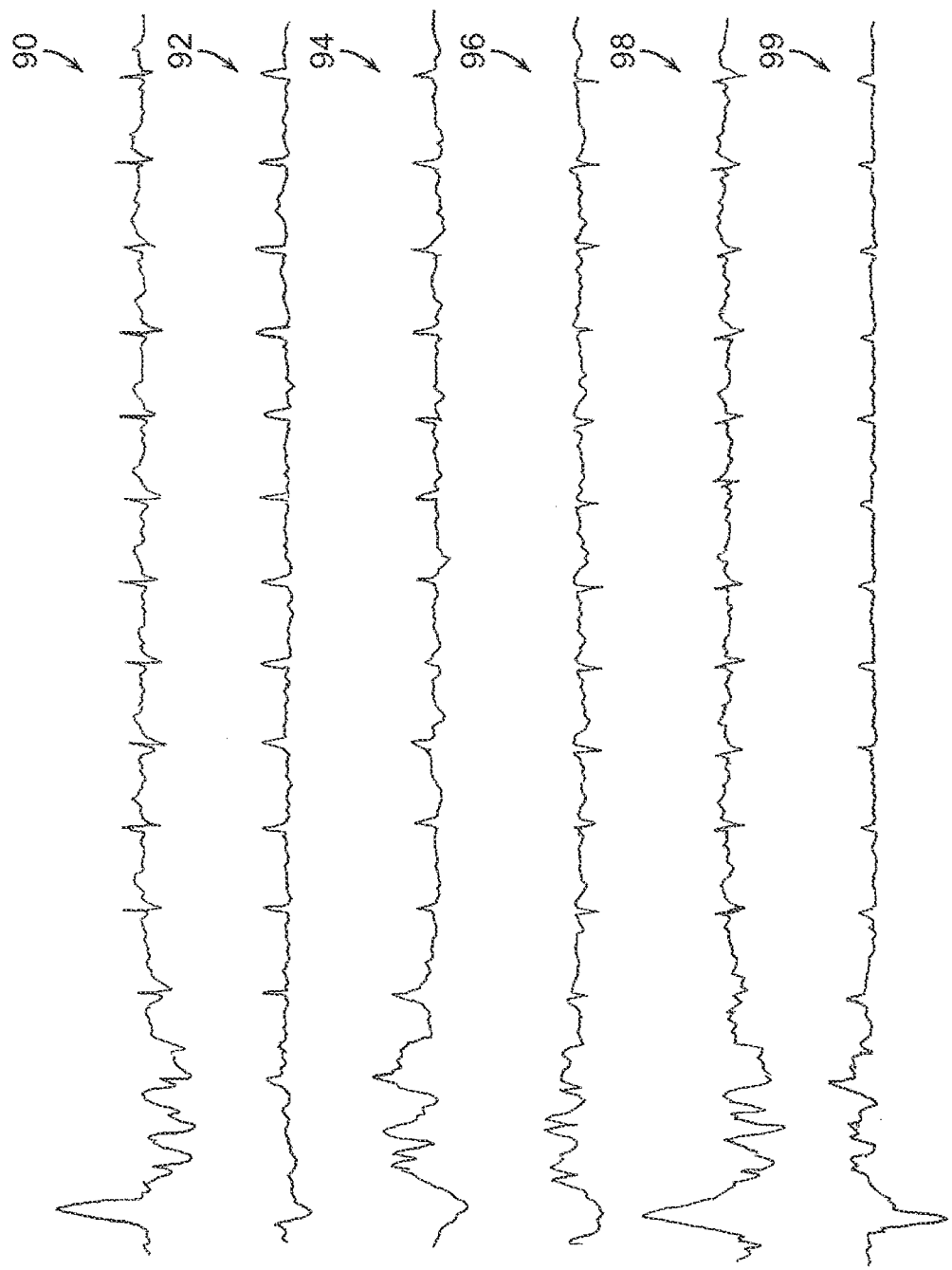

The same subject was retested with Kendall Q-Trace electrodes from Tyco Healthcare Retail Services AG Corporation of Switzerland using an ionically conductive hydrogel system on a polyester film with a silver/silver chloride coating over a conductive carbon coating, to receive the signal picked up by the hydrogel. The sensor outputs are provided to the ECG monitor, and signals from the I, II, and III leads, as well as signals from the AVR, AVL and AVF leads are shown at 90, 92, 94, 96, 98 and 99 respectively in FIG. 8B for the same subject using a hydrogel of the prior art. Comparisons of the two sets of ECG traces in FIGS. 8A and 8B show substantially the same signal fidelity.

As discussed above, another benefit of systems of the invention is the ability of the adhesive to cover in a continuous fashion two or more sensing electrodes. The SRM is not discreet with respect to a single electrode, but instead spans across, in the X, Y plane, several electrodes and still permits a strong, unique signal to be passed through the electrodes in the Z dimension. A series of tests were run to measure this effect.

Figure 9:
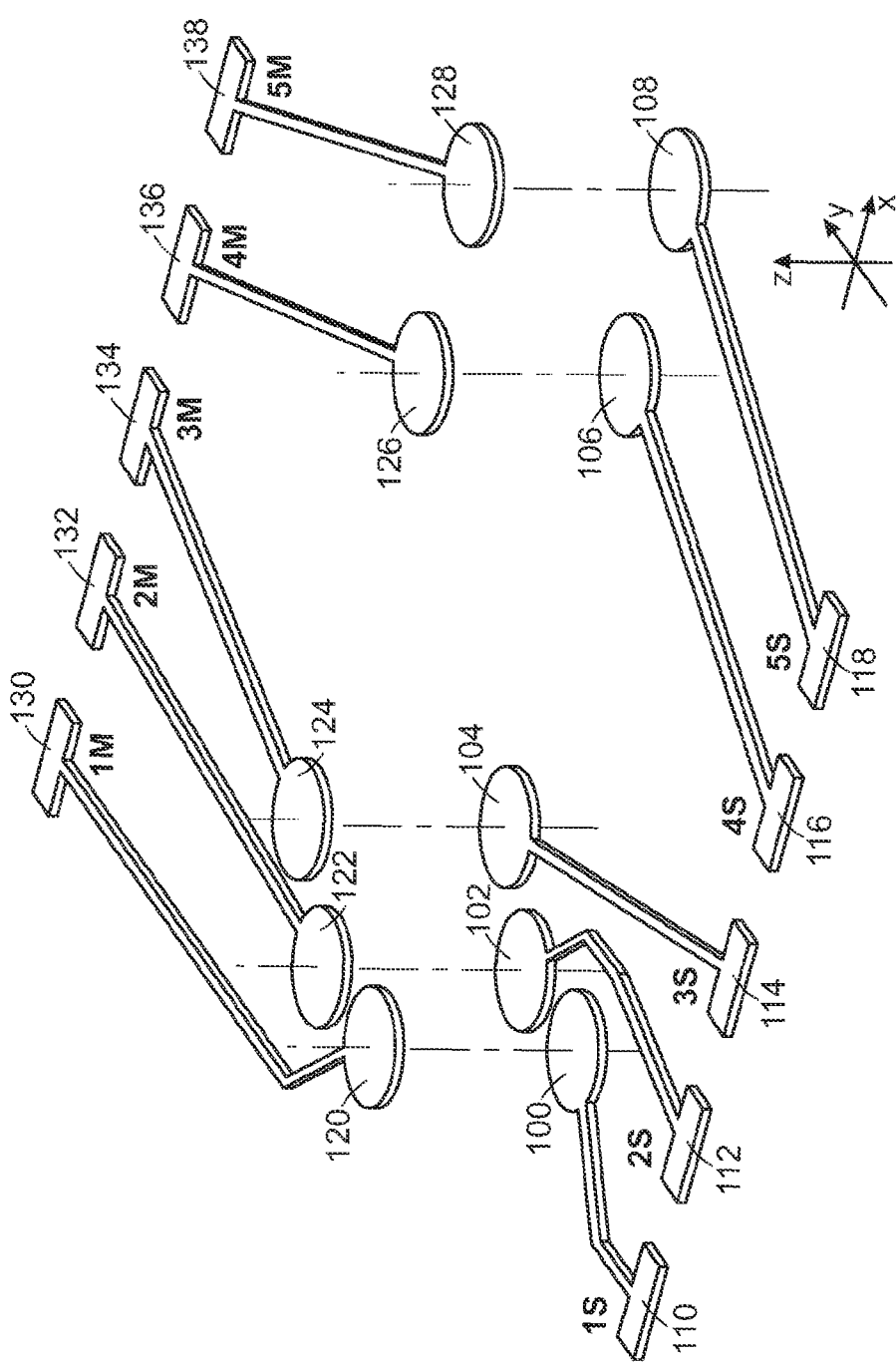
FIG. 9 shows an illustrative diagrammatic view of an electrode test fixture system employed for testing systems of the invention.

A test fixture of electrodes was provided as shown in FIG. 9. The test system also included a Spacelabs Model #514 Patient Monitor as sold by Spacelabs, Inc. of Chatsworth, Calif. as a common source of the test signals, as well as a GE Medical System Model #MAC 1200 as sold by General Electric of Schenectady, N.Y. for the signal receiver. As shown in FIG. 9, the test fixture of electrodes includes a first set of electrodes 100, 102, 104, 106 and 108 that are connected to the source via source high impedance connectors 110, 112, 114, 116 and 118 respectively, and a second set of electrodes 120, 122, 124, 126 and 128 that are connected to the monitor via high impedance monitor connectors 130, 132, 134, 136 and 138 respectively. The SRM material being tested is placed between the first set of electrodes and the second set of electrodes.

Separate signals were applied at source connections 2S (to electrode 102) and 3S (to electrode 104). Test samples were placed in direct physical contact with both the source and monitor connections so that the source signals could transmit through the test samples and be received at monitoring connections 2M (electrode 122) and 3M (electrode 124). The electrode pairs (100, 120), (102, 122), (104, 124), (106, 126) and (108, 128) comprised five electrode pairs that are designed to be placed at certain conventional locations on a human subject for measuring signals from a patient's heart. The sensor outputs are provided to an ECG monitor, and the monitor may provide a composite heart signal, and/or may provide discrete signals representing certain portions of a composite signal, including for example, the traditionally used ECG signals from the I, II, and III leads and from the AVR, AVL and AVF leads.

Five tests were conducted as follows. Test 1 provided a control in that the first and second sets of electrodes were on contact with one another. Test 2 provided a second control that employed a conventional hydrogel material located between the electrodes such that neighboring electrodes (e.g., 100 and 102) were provided with discrete regions of hydrogel. Test 3 provided a third control that employed an SRM as disclosed above that was located between the electrode pairs but was not common to more than one source or monitor electrode. Test 4 employed a large area of an SRM as discussed above that spanned across all electrode pairs. For example, the SRM between electrodes 102 and 122 was also between electrodes 104 and 124 in a continuous film. Test 5 employed a conventional hydrogel that spanned across all electrode pairs.

Figure 10A:
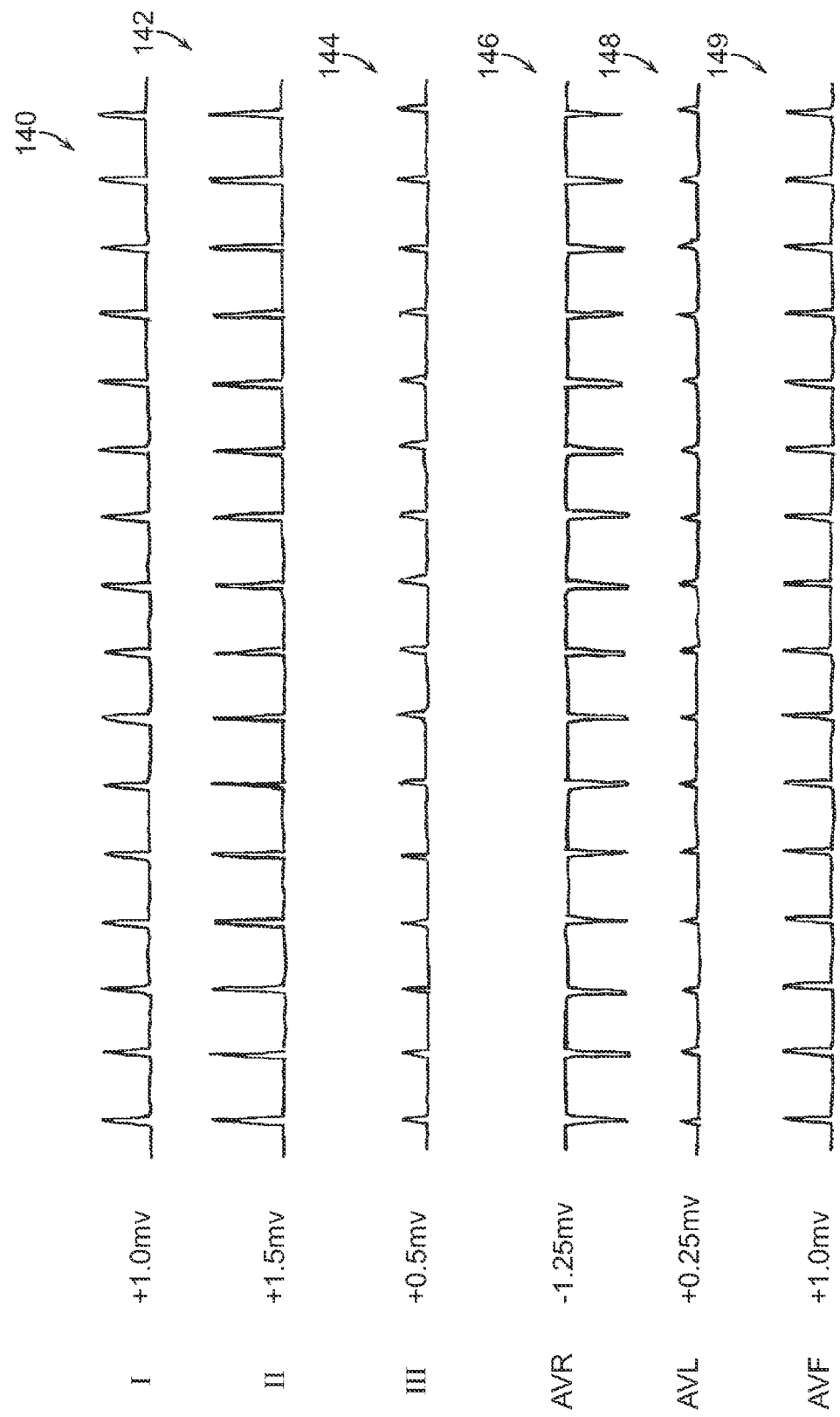
FIGS. 10A-10E show illustrative graphical representations of ECG I, II, II AVR, AVL and AVF signals obtained for purposes of testing multiple electrode systems in accordance with a further embodiment of the invention.
Figure 10B:
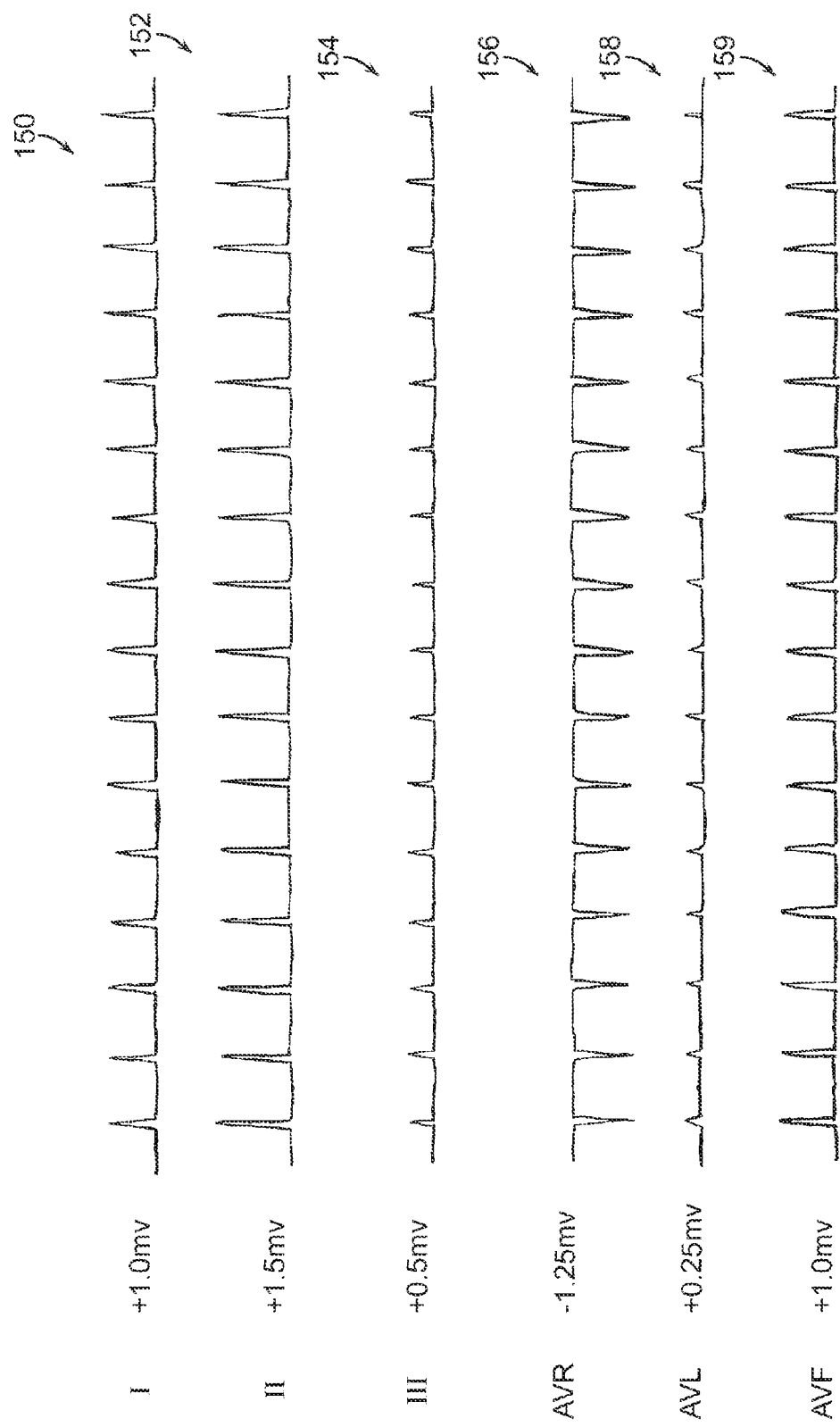
Figure 10C:
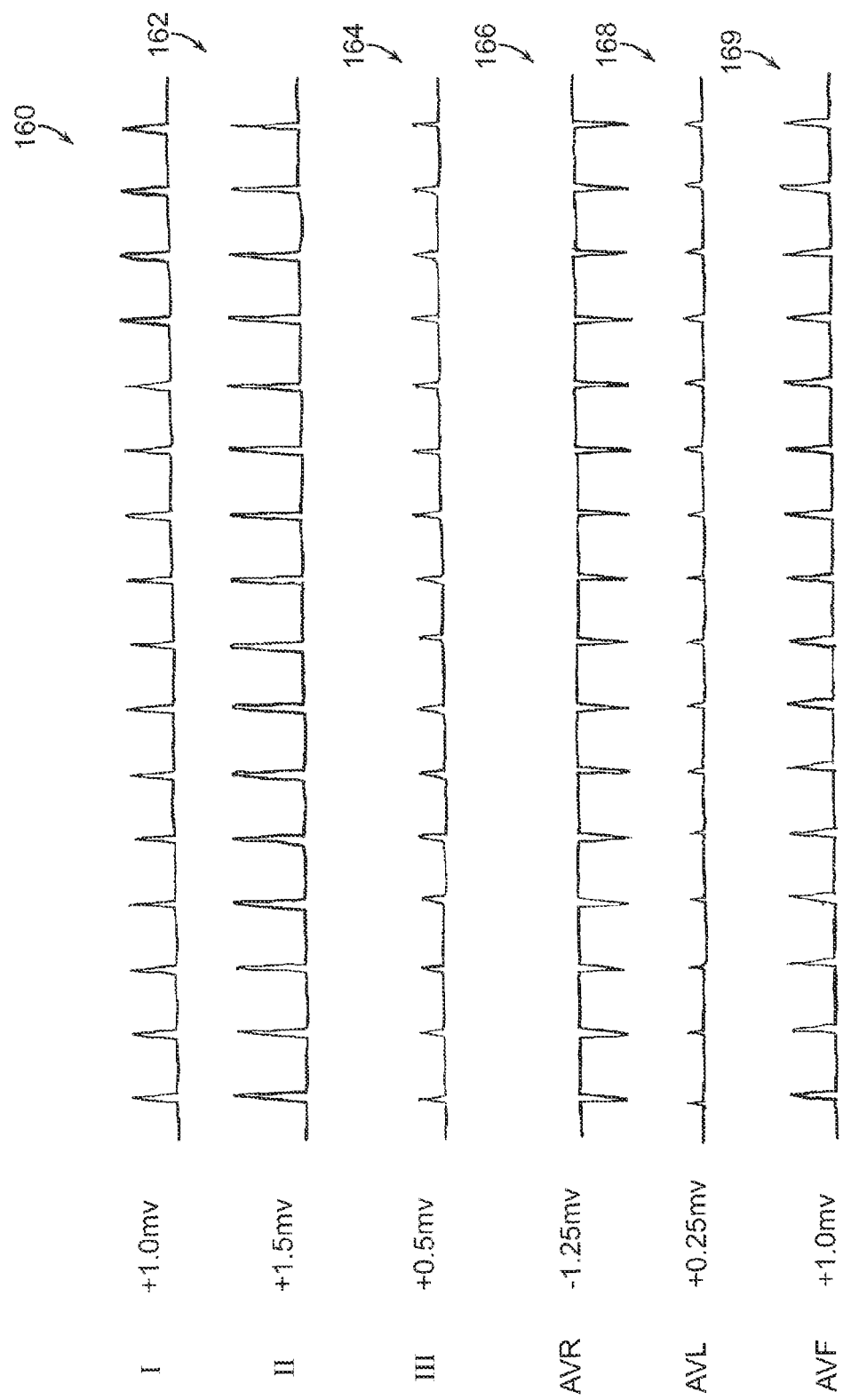
Figure 10D:
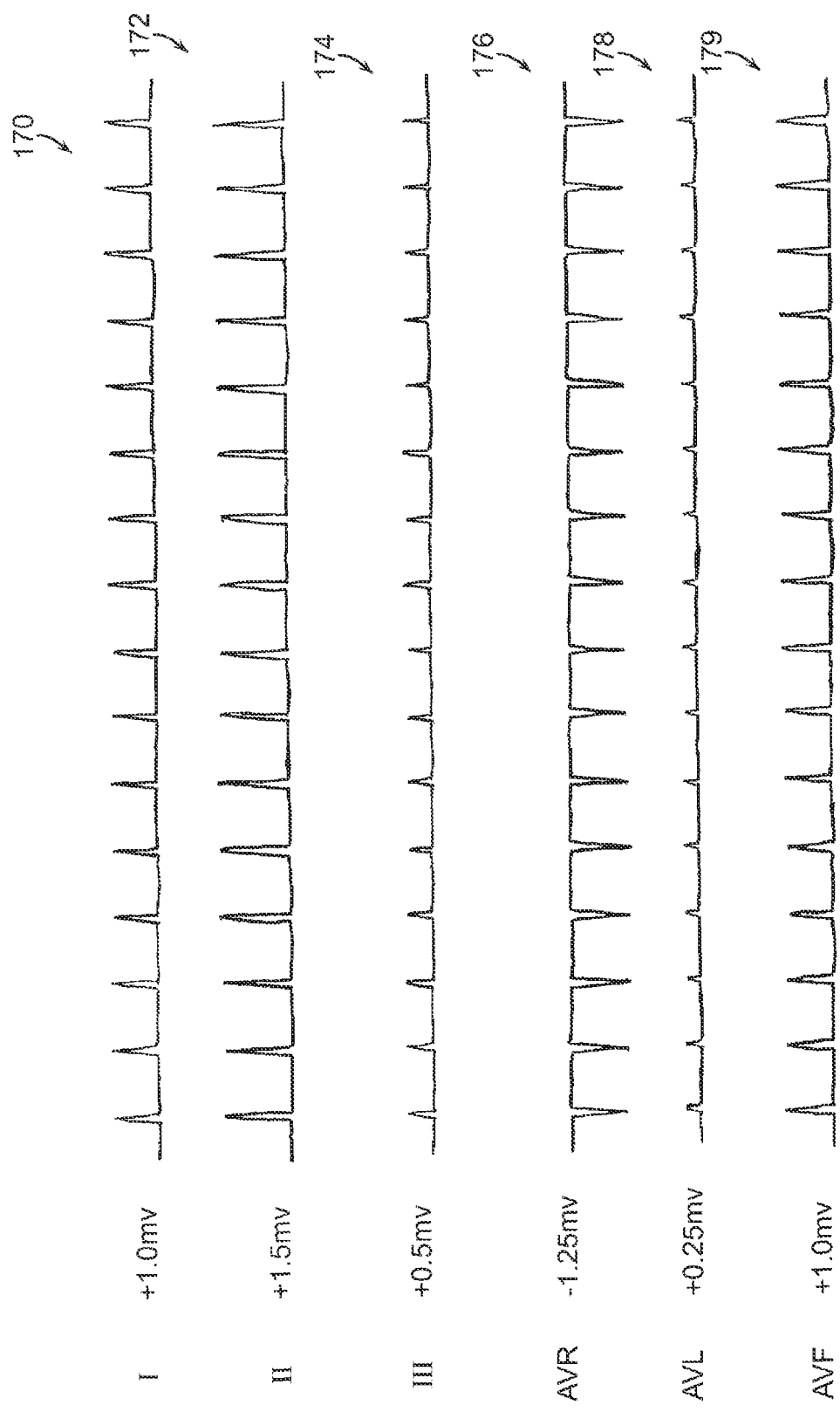
Figure 10E:
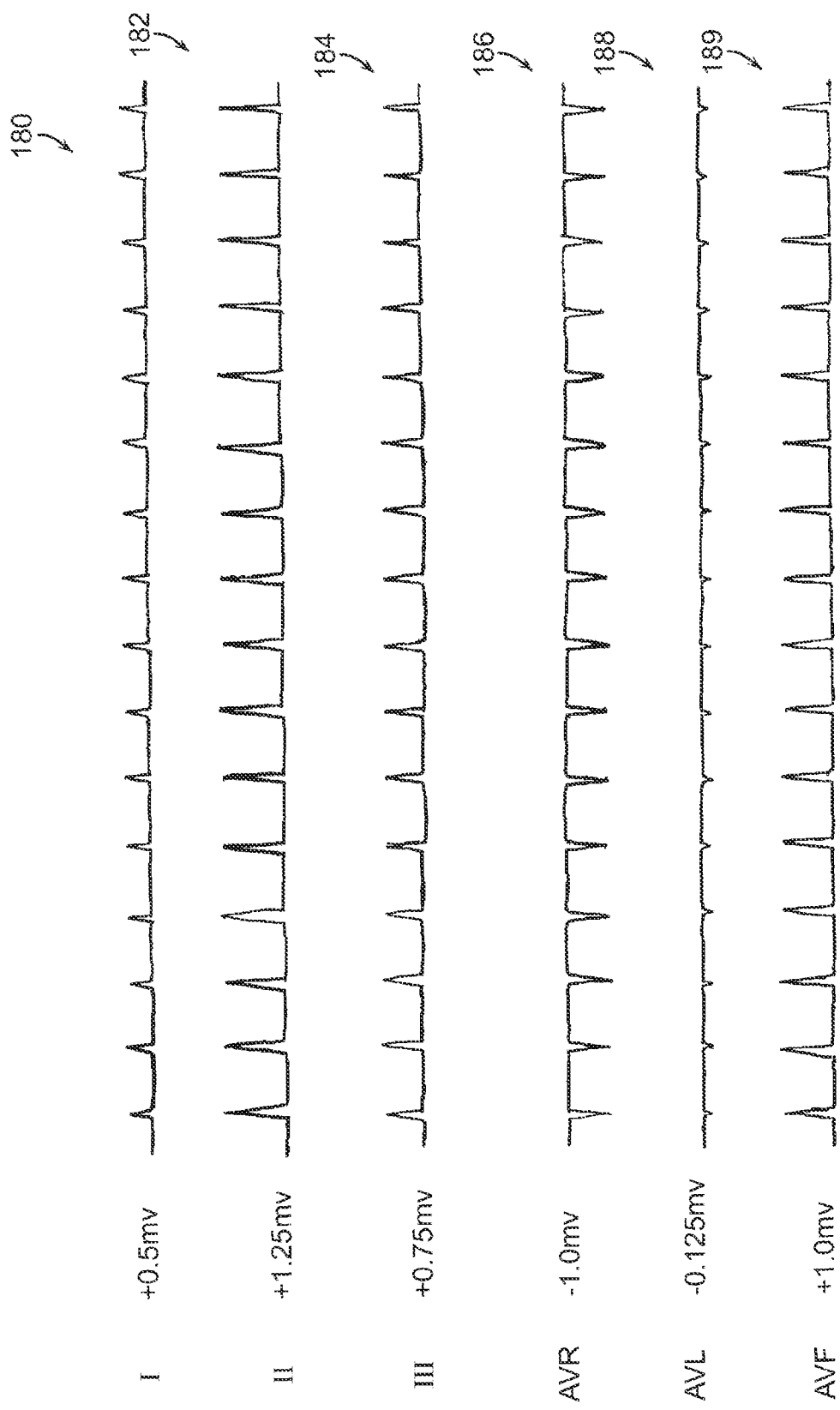

FIG. 10A shows the outputs of the I, II, III, AVR, AVL and AVF leads at 140, 142, 144, 146, 148 and 149 respectively for the control system (test 1) that includes no SRM material between each pair of electrodes. FIG. 10B shows the outputs of the I, II, III, AVR, AVL and AVF leads at 150, 152, 154, 156, 158 and 159 respectively for the control system (test 2) that includes a discrete portion of hydrogel material between each pair of electrodes. FIG. 10C shows the outputs of the I, II, III, AVR, AVL and AVF leads at 160, 162, 164, 166, 168 and 169 respectively for the control system (test 3) that includes a discrete portion of SRM material in accordance with the invention between each pair of electrodes. FIG. 10D shows the outputs of the I, II, III, AVR, AVL and AVF leads at 170, 172, 174, 176, 178 and 179 respectively for the system (test 4) that includes a continuous SRM material of the invention spanning across the area between each of the pairs of electrodes. FIG. 10E shows the outputs of the I, II, III, AVR, AVL and AVF leads at 180, 182, 184, 186, 188 and 189 respectively for the system (test 5) that includes a continuous hydrogel material of the prior art spanning across the area between each of the pairs of electrodes.

As may be seen in FIGS. 10A-10C, the standard ECG signals are very similar to one another for each of the control tests (tests 1-3) mentioned above. The system that employed a continuous SRM material of the invention (as shown in FIG. 10D) also provided standard I, II, III, AVR, AVL and AVF lead signals that were similar to those of FIGS. 10A-10C. The system of FIG. 10E, however, that employed a continuous hydrogel material of the prior art across each of the pairs of electrodes, produced lead I, lead III, lead AVR, and lead AVL signals of a much lower amplitude, and the polarity of the AVL signal was reversed. It is understood that this is because certain electrodes detected signals that were not immediately adjacent those electrodes, due at least in part to the fact that the common hydrogel material is conductive, not capacitive. Any effort to analyze such lead signals in an ECG system would result in incorrect (and possibly dangerously incorrect) readings. The system of FIG. 10D, however, functioned well even though a single continuous film of the SRM material was used for each of the pairs of electrodes.

This demonstrated another huge advantage of the SRM, with high internal impedance. Thus a multi-sensor composite, such as discussed above may be constructed with each sensor electrode covered by a continuous layer of an SRM without loss of point signal fidelity. Such a device would have numerous uses in medical and non-medical monitoring and/or diagnostic applications.

Adhesive peel strengths of a prior art Hydrogel and examples of composites of the invention were tested as follows.

Sample 1 was a conventional Kendall Q-Trace Gold 5500 Hydrogel material (sold by Covidien AG Corporation of Switzerland), and was 0.013 inches (330 microns) thick by 9 square inches (0.0117 cubic inches).

Sample 2 was a signal receptive material (SRM) that included FLEXcon EXH-585 acrylic adhesive (sold by FLEXcon Company, Inc. of Spencer, Mass.) including 20% by weight of ARAQUAD 2HT-75 quaternary ammonium salt (sold by Akzo Nobel Surface Chemistry LLC of Chicago, Ill.). The acrylic adhesive and salt exhibited a balanced inter-molecular attraction to themselves and each other such that the salt remained suspended within the acrylic adhesive without blooming or crystallizing. Sample 2 was 0.001 inches (25 microns) thick by 6 square inches (0.0006 cubic inches).

Sample 3 was an SRM that included FLEXcon EXH-585 acrylic adhesive including 20% by weight of ARAQUAD 2HT-75 quaternary ammonium salt, and was 0.002 inches (50 microns) thick by 6 square inches (0.0012 cubic inches).

Sample 4 was an SRM that included FLEXcon EXH-585 acrylic adhesive including 20% by weight of ARAQUAD 2HT-75 quaternary ammonium salt, and was 0.001 inches thick by 1.4 square inches (0.0014 cubic inches).

Sample 5 was an SRM that included FLEXcon EXH-585 acrylic adhesive including 20% by weight of ARAQUAD 2HT-75 quaternary ammonium salt, and was 0.002 inches thick by 1.4 square inches (0.0028 cubic inches).

Peel strengths were recorded for peak force (in grams) and the total energy (gram seconds) was recorded at a rate of travel of 12 inches per minute. The testing apparatus was a Stable Micro Systems TA XTPlus Texture Analyzer (sold by Stable Micro Systems Ltd of England), and the data capture speed was 400 data points per second. The results of the tests (run ten times each) using peel strengths on stainless steel panels at 180 degrees are shown in Table 1.

TABLE 1

| Sample | Peak Force (grams) | Total Energy (gram seconds) |
|---|---|---|
| Sample 1 (0.0117 in$^3$ Hydrogel) | 708, 758, 918, 1123, 976, 1121, 1478, 943, 1082, 1170 Average: 1027 | 5222, 6036, 5907, 7393, 7129, 6847, 8949, 5671, 6532, 7800 Average: 6749 |
| Sample 2 (0.0006 in$^3$ SRM) | 1304, 1177, 953, 1363, 1455, 1671, 1529, 1081, 1503, 1416 Average: 1345 | 5741, 5446, 5001, 6481, 7280, 7525, 6675, 5493, 7538, 7637 Average: 6482 |
| Sample 3 (0.0012 in$^3$ SRM) | 1262, 1307, 1012, 1367, 1615, 1663, 1552, 1757, 1653, 1543 Average: 1473 | 6621, 6927, 5401, 6219, 1950, 8487, 7353, 9005, 8408, 7620 Average: 7339 |
| Sample 4 (0.0014 in$^3$ SRM) | 2075, 1813, 1739, 1657, 1981, 1817, 1785, 1539, 1723, 1385 Average: 1751 | 14297, 13078, 11232, 11555, 13693, 13521, 12780, 10789, 13872, 12366 Average: 12718 |
| Sample 5 (0.0028 in$^3$ SRM) | 2452, 2120, 2269, 2244, 1589, 1680, 1538, 1663, 1740, 1929 Average: 1922 | 16409, 15357, 17349, 15223, 13393, 11049, 13081, 11850, 13834, 14328 Average: 14187 |

As may be seen in Table 1, although the samples of the SRM material used were much smaller in cubic area, the adhesive characteristics were far greater. Even with a much smaller bonding area (0.6 sq inches versus 0.9 sq inches), the SRM material at 1 mil (Sample 2) has better adhesion than the 13 mil Hydrogel (Sample 1), and (within statistical measurement variation) has comparable total energy values. The SRM material at 2 mil and 1.4 sq inches (Sample 5) has significantly better adhesion. The adhesive material may, therefore, have a thickness of less than about 50 microns yet provide a total peel strength of at least about 6000 gram seconds. For comparative purposes (and for the limited number of data points) the areas were normalized for all samples to 1 sq inch as shown in Table 2.

TABLE 2

| Sample | Peak Force (grams) | Total Energy (grams second) |
|---|---|---|
| Sample 1 (0.0117 in$^3$ Hydrogel) | Average: 1,140 | Average: 7,500 |
| Sample 2 (0.0006 in$^3$ SRM) | Average: 2,240 | Average: 10,800 |
| Sample 3 (0.0012 in$^3$ SRM) | Average: 2,450 | Average: 12,230 |
| Sample 4 (0.0014 in$^3$ SRM) | Average: 1,250 | Average: 9,080 |
| Sample 5 (0.0028 in$^3$ SRM) | Average: 1,372 | Average: 10,130 |

The SRM material, therefore, provides improved adhesion using thinner material, and the material may be provided over a wider area to increase the bond area. Because the SRM material is also a high impedance dielectric material (and therefore is specific to the area of the signal site in a patient), the bond area may be provided over a considerable area and may further be common to multiple electrodes as discussed above.

The stiffness of certain of the samples were also tested as follows using a Thwing Albert Handle-O-Meter model 211-5 (as sold by the Thwing-Albert Instrument Co. of Philadelphia, Pa.) using Teflon plates at a plate gap of ¼ inch. The composites of Samples 1, 4 and 5 were tested on a ½ inch wide film of 3 mil white polyester (a FLEXcon PM300W (md) as sold by FLEXcon Company, Inc. of Spencer, Mass.). The stiffness of the each of these samples as well as the stiffness of the film by itself were tested ten times each, and the results are shown in Table 3.

TABLE 3

| Sample | Stiffness | Stiffness (grams per inch) |
|---|---|---|
| Sample 1 (0.0117 in$^3$ Hydrogel) | 66.2, 63.0, 60.5, 61.5, 65.4, 62.1, 64.3, 60.7, 58.5, 67.0 Average: 62.9 | Average: 125.8 |
| Sample 4 (0.0014 in$^3$ SRM) | 51.2, 51.2, 55.7, 54.3, 55.1, 53.6, 56.0, 55.6, 58.9, 57.1 Average: 54.9 | Average: 109.7 |
| Sample 5 (0.0028 in$^3$ SRM) | 55.4, 54.0, 55.8, 54.7, 53.6, 54.3, 54.5, 55.8, 55.5, 54.6 Average: 54.8 | Average: 109.6 |
| 0.3 mil film of polyester | 38.1, 37.3, 37.6, 38.3, 38.9, 38.2, 39.8, 37.5, 38.2, 37.5 Average: 38.1 | Average: 76.3 |

It is clear that each of the Samples 1, 4 and 5 contribute to the overall stiffness (as compared with the 0.3 mil film of polyester by itself), and that the Samples 4 and 5 provide stiffness values that are comparable to those of the prior art Hydrogel (Sample 1).

Figure 11:
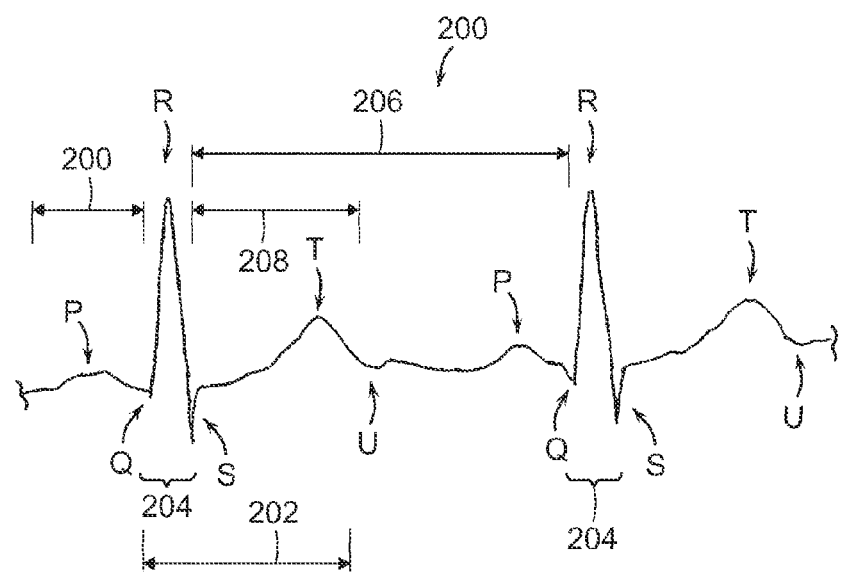
FIG. 11 shows an illustrative diagrammatic view of a portion of a waveform of an ECG signal in a system of an embodiment of the invention.

As shown in FIG. 11, a typical ECG signal 200 of a human heart should include several characteristic features that are repeated at the heart beat repetition rate. The regions are conventionally referred to as a P region, a Q region, an R region, an S region, a T region and a U region as shown. Portions of the signal that are typically analyzed include a QT region as shown at 202, a QRS region as shown at 204, an RR region as shown at 206 and an ST region as shown at 208. Signals provided by systems of the invention may be analyzed by conventional ECG analytical methodologies to identify abnormalities or other problems with a heart.

In accordance with further embodiments of the invention, however, sensor systems may be employed that include multiple sensors on a single dielectric material, and the multiple sensors may be placed over a patient's heart such that a large number of discrete electrodes (e.g., an array of 100 electrodes or more) are provided that cover the area of interest of a patient. This means that a technician may not be required to find exactly the correct location for each of a small number of electrodes as is conventionally done. The technician instead may place over a patient's chest the array of electrodes all coupled to the same dielectric material. The array may, for example, be connected through a via to a wiring grid to transmit the signal or they may be transmitted wirelessly. In further embodiments, an array of electrodes may be placed of each of the areas that conventionally receive a single electrode. The technician may then find the electrode for each area of interest that is yielding the strongest signals to provide, for example, each of the conventional I, II, III, AVR, AVL and AVF signals.

Figure 12:
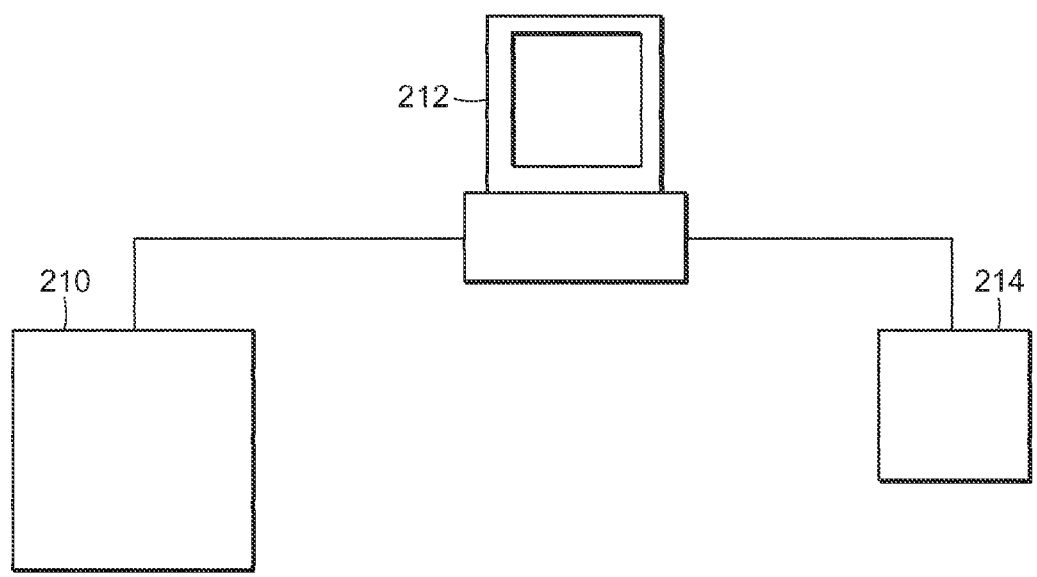
FIG. 12 shows an illustrative diagrammatic view of measurement and analysis components of a system in accordance with an embodiment of the invention.

As shown in FIG. 12, a multi-electrode system 210 may be coupled to a processing system 212 that receives signals from each of the electrodes (either selectively or together). The processing system 212 may then determine if the chosen electrodes are at the optimal viewing angle for signal detection and which of the (for example six) electrodes will be used in conducting the analysis of the subject. The system may then conduct an automated analysis, and then produce an output to an output device 214 that may be either a display device or printer.

Figure 13:
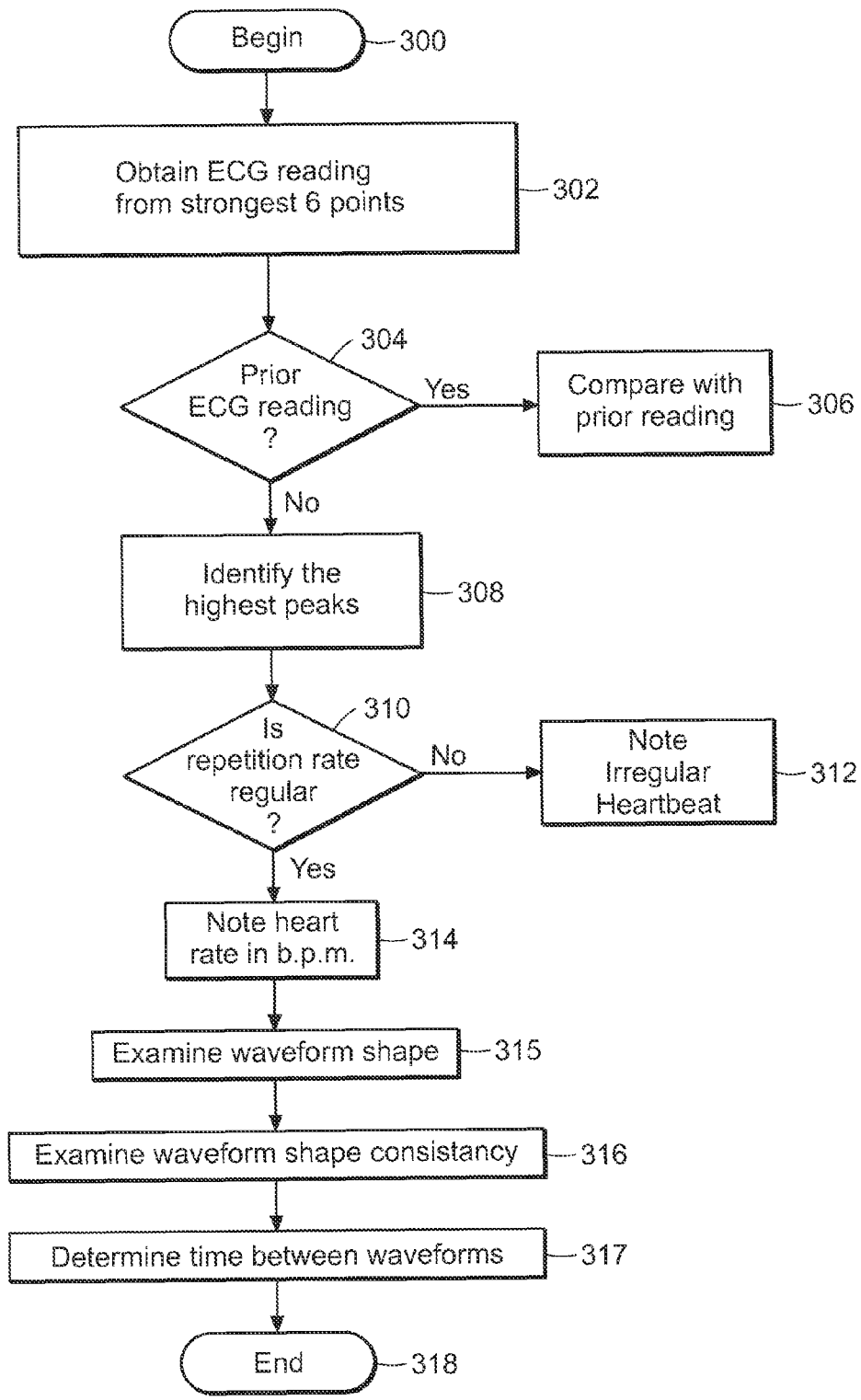
FIG. 13 shows a diagrammatic flow chart of analysis steps employed in an automated system of an embodiment of the invention.

For example, as shown in FIG. 13, such an automated process may first begin (step 300) by obtaining an ECG set of values from the six data points that yield the signals with the least noise, and or the strongest amplitude signals (step 302). In other embodiments, the system may select the electrodes of an array based on other factors such as a known heart size and/or physiology, or a fixed distance from a particular datum point.

For example, the system could then determine (step 304) whether a prior reading exists in the storage system for that particular patient. If so, the system could compare the new signals to the prior signals (step 306). The system could then identify the signals with the largest slopes, highest peaks (step 308) and assume that these are the R regions. If these peaks are not consistent (step 310), the system indicates that the heart rate is irregular (step 312), and if the peaks are consistent within a range of, for example, 5%, the system will note a heart rate in beats per minute (step 314).

Further analysis may examine the waveform shape (step 315), waveform consistency (step 316) and the time between waveforms (step 317) to determine the functionality of the heart's conduction system prior to ending (step 318). Many cardiac conditions have characteristic patterns on the ECG. These arrhythmias are valuable clues to diagnosing and treating cardiac illnesses—acute and chronic.

Through such ECG analysis using a multi-sensor system, it is possible to trace the conduction through the heart, estimate the size and orientation of the heart, and even to locate regions of the heart which have suffered injury, ischemia (oxygen deprivation), or necrosis (tissue death).

Analyses may include for example, determining whether: the heart rate is fast or slow, the atrial and ventricular rates the same, the P-P interval and the R-R interval are regular or irregular, if the rhythm is irregular is it consistent or irregular irregularity, is there a P-wave before each QRS, is there a QRS before every P-wave, are the P-waves and QRS complexes identical and normal in configuration, are the P-R and QRS intervals within normal limits, etc.

Those skilled in the art will appreciate that numerous modifications and variations may be made to the above disclosed embodiments without departing from the spirit and scope of the invention.

What is claimed is:

1. A method of detecting a time varying signal from a subject, said method comprising the steps of: applying a first surface of a polymeric material to a subject, wherein said polymeric material is anisotropic and includes a polar material that is responsive to the presence of an alternating electric field, said polymeric material having at least two electrodes on a second surface thereof that is opposite the first surface; and receiving a time varying signal at a first electrode of the at least two electrodes at a first location, wherein the time varying signal is not received at a second electrode of the at least two electrodes.

2. The method as claimed in claim 1, wherein said polymeric material is an adhesive.

3. The method as claimed in claim 1, wherein said at least two electrodes are part of an array of electrodes that are provided on the polymeric material.

4. A method of detecting a time varying signal from a patient, said method comprising the steps of: applying a first surface of an adhesive material to a patient, wherein said adhesive material is anisotropic and is provided at a thickness of less than about 500 microns yet provides total peel strength of at least about 600 gram/inch, said adhesive material including a polar material that is responsive to the presence of an alternating electric field; and receiving a time varying signal at a first electrode that is in contact with a second surface of the adhesive material that is opposite the first surface, and not receiving the time varying signal at a second electrode that is in contact with the second surface of the adhesive.

5. The method as claimed in claim 4, wherein said first and second electrodes are part of an array of electrodes.

6. The method as claimed in claim 5, wherein said method further includes the steps of detecting any input signals from the array of electrodes, and selecting certain signals for further analysis in an ECG system.

7. A method of detecting a time varying signal from a subject, said method comprising the steps of: receiving the time varying signal from the subject at a first side of an anisotropic polymeric material, said anisotropic polymeric material including a polar material that is responsive to the presence of an alternating electric field; and providing a first output signal to a first conductive electrode on an opposing second side of the polymeric material, while not providing the first output signal to a second conductive electrode on the opposing second side of the polymeric material responsive to the first time varying signal even though the polymeric material is contiguous with both the first and second conductive electrodes.

8. The method as claimed in claim 7, wherein said polymeric material is an adhesive.

9. The method as claimed in claim 7, wherein said polar material aligns within the polymeric material in the presence of the time varying signal from the subject.

10. The method as claimed in claim 7, wherein said first and second conductive electrodes are part of an array of conductive electrodes on the polymeric material.

11. The method as claimed in claim 7, wherein said first and second conductive electrodes are provided within an ECG harness of a plurality of conductive electrodes in contact with the polymeric material such that the dielectric material is contiguous with each of a plurality of conductive electrodes in the ECG harness of conductive electrodes.

12. The method as claimed in claim 7, wherein said polymeric material is provided at a thickness of less than about 500 microns.

13. The method as claimed in claim 7, wherein said method further includes the step of providing the first output signal from the first conductive electrode to a monitor system via a conductive path.

14. A method of detecting a time varying signal from a subject, said method comprising the steps of: receiving the time varying signal from the subject at a first side of a contiguous polymeric material, said contiguous polymeric material being anisotropic and including a polar material; permitting a first set of polar material within the contiguous polymeric material to undergo a change responsive to the presence of the time varying signal from the subject, while a second set of polar material within the contiguous polymeric material does not undergo the change; and providing a first output signal from a first conductive electrode that is proximate the first set of polar material responsive to the time varying signal from the subject, and not providing the first output signal from a second conductive electrode that is proximate the second set of polar material.

15. The method as claimed in claim 14, wherein said polymeric material is an adhesive.

16. The method as claimed in claim 14, wherein said first conductive electrode and the second conductive electrode are part of an array of conductive electrodes on the dielectric material.

17. The method as claimed in claim 14, wherein said polymeric material includes a polar material that aligns within the polymeric material in the presence of the time varying signal from the subject.

18. The method as claimed in claim 14, wherein said first conductive electrode and the second conductive electrode are provided within an ECG harness of conductive electrodes in contact with the polymeric material such that the polymeric material is contiguous with each of a plurality of conductive electrodes in the ECG harness of conductive electrodes.

19. The method as claimed in claim 14, wherein said method further includes the step of providing the first output signal from the first conductive electrode to a monitor system via a conductive path.

\* \* \* \* \*